US005249702A

United States Patent [19]

Topp et al.

[11] Patent Number: 5,249,702

[45] Date of Patent: Oct. 5, 1993

[54] BEVERAGE CONTAINER AND SUPPORT BRACKET THEREFORE

[76] Inventors: Kathy R. Topp; W. Lawrence Topp, both of 8806 LaPrada Ct., Elk Grove, Calif. 95624

[21] Appl. No.: 825,494

[22] Filed: Jan. 24, 1992

[51] Int. Cl.[5] .................. A47G 19/22; B65D 51/18; A61K 9/22; A47K 1/08

[52] U.S. Cl. .................. 220/705; 224/42.45 R; 224/42.46 R; 224/148; 220/478; 220/476; 220/254; 220/230; 215/229; 248/311.2; 248/690; 248/214; 604/890.1; 604/416; 604/82; 604/85

[58] Field of Search .................. 248/311.2, 690, 214; 224/42.45 R, 42.46 R, 148; 220/737, 705, 478, 230, 254; 215/11.1, 229, 228; 604/890.1, 891.1, 892.1, 416, 82, 85

[56] References Cited

U.S. PATENT DOCUMENTS

| | | | |
|---|---|---|---|
| 2,992,804 | 7/1961 | Doran | 248/311.2 |
| 4,133,443 | 1/1979 | Medina et al. | 248/311.2 X |
| 4,607,755 | 8/1986 | Andreozzi | 224/148 X |
| 4,776,623 | 10/1988 | Manning | 224/42.45 R X |
| 4,821,895 | 4/1989 | Roskilly | 215/11.1 |
| 4,825,590 | 5/1989 | Cullinane | 248/311.2 X |
| 4,858,869 | 8/1989 | Stang | 248/311.2 |
| 4,928,876 | 5/1990 | Marshall | 224/42.45 R X |
| 5,048,705 | 9/1991 | Lynd et al. | 220/709 X |
| 5,069,671 | 12/1991 | Theeuwes | 604/85 X |

*Primary Examiner*—Allan N. Shoap
*Assistant Examiner*—Paul A. Schwarz
*Attorney, Agent, or Firm*—Hugh E. Smith

[57] ABSTRACT

A beverage container includes a cylindrical container formed with a mounting bracket fixedly secured to a wall of the container for securement to a support plate portion, with the support plate portion including a mounting head received within the bracket. A modification of the invention includes a lid structure arranged to receive the cylinder formed with a matrix of apertures directed therethrough, with a saturated sponge including a nutrient fluid contained therewithin to permit the nutrient fluid to be directed into a surrounding drinking fluid within the container. A plurality of such nutrient cylinders are arranged for mounting within an associated support container arranged for transport by an individual in association with the drinking container of the invention.

2 Claims, 5 Drawing Sheets

BEVERAGE CONTAINER AND SUPPORT BRACKET THEREFORE

BACKGROUND OF THE INVENTION

1. Field of the Invention

The field of invention relates to drinking container apparatus, and more particularly pertains to a new and improved beverage container apparatus wherein the same is arranged for the ease of transport of the container during use.

2. Description of the Prior Art

Drinking containers of various types are utilized throughout the prior art to transport various drinking fluids therewithin for use by individuals permitting ease of transport of such fluid. Prior art structure arranged for the support of various fluids such as within a motor vehicle is arranged and set forth in U.S. Pat. No. 4,728,018 to Parker wherein a holder structure is pivotally mounted to a support bracket positioned within a vehicle.

U.S. Pat. No. 4,953,771 to Fischer, et al. sets forth a further example of a drawer mounted cup holder arranged for positioning within a vehicle.

Accordingly, it may be appreciated that there continues to be a need for a new and improved beverage container apparatus as set forth by the instant invention which addresses both the problems of ease of use as well as effectiveness in construction in permitting vehicular support of the organization in use and in this respect, the present invention substantially fulfills this need.

SUMMARY OF THE INVENTION

In view of the foregoing disadvantages inherent in the known types of beverage container apparatus now present in the prior art, the present invention provides a beverage container apparatus wherein the same is arranged for securement within a vehicle or securement relative to an individual in use. As such, the general purpose of the present invention, which will be described subsequently in greater detail, is to provide a new and improved beverage container apparatus which has all the advantages of the prior art beverage container apparatus and none of the disadvantages.

To attain this, the present invention provides a beverage container including a cylindrical container formed with a mounting bracket fixedly secured to a wall of the container for securement to a support plate portion, with the support plate portion including a mounting head received within the bracket. A modification of the invention includes a lid structure arranged to receive the cylinder formed with a matrix of apertures directed therethrough, with a saturated sponge including a nutrient fluid contained therewithin to permit the nutrient fluid to be directed into a surrounding drinking fluid within the container. A plurality of such nutrient cylinders are arranged for mounting within an associated support container arranged for transport by an individual in association with the drinking container of the invention.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved beverage container apparatus which has all the advantages of the prior art beverage container apparatus and none of the disadvantages.

It is another object of the present invention to provide a new and improved beverage container apparatus which may be easily and efficiently manufactured and marketed.

It is a further object of the present invention to provide a new and improved beverage container apparatus which is of a durable and reliable construction.

An even further object of the present invention is to provide a new and improved beverage container apparatus which is susceptible of a low cost of manufacture with regard to both materials and labor, and which accordingly is then susceptible of low prices of sale to the consuming public, thereby making such beverage container apparatus economically available to the buying public.

Still yet another object of the present invention is to provide a new and improved beverage container apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
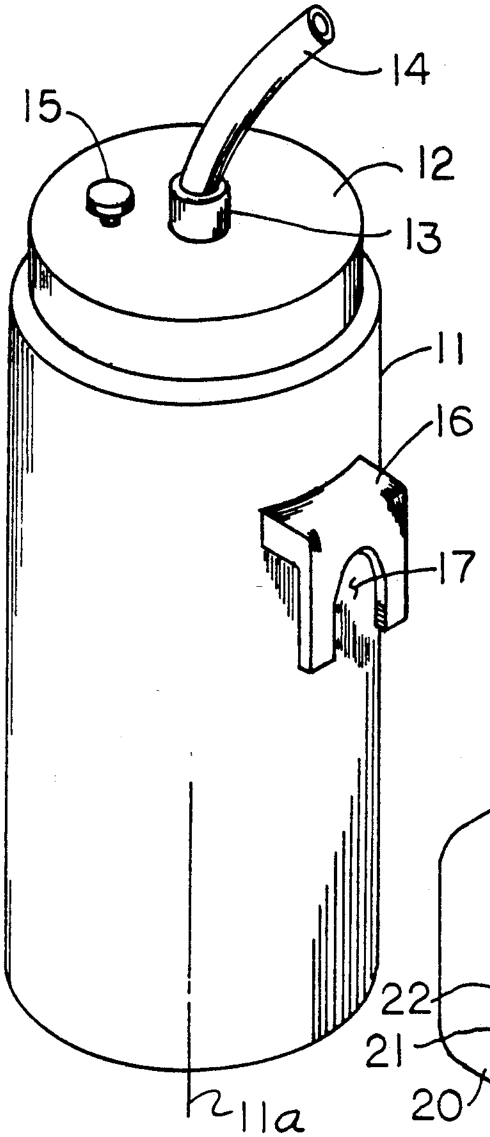
FIG. 1 is an isometric illustration of the container structure of the invention.
Figure 2:
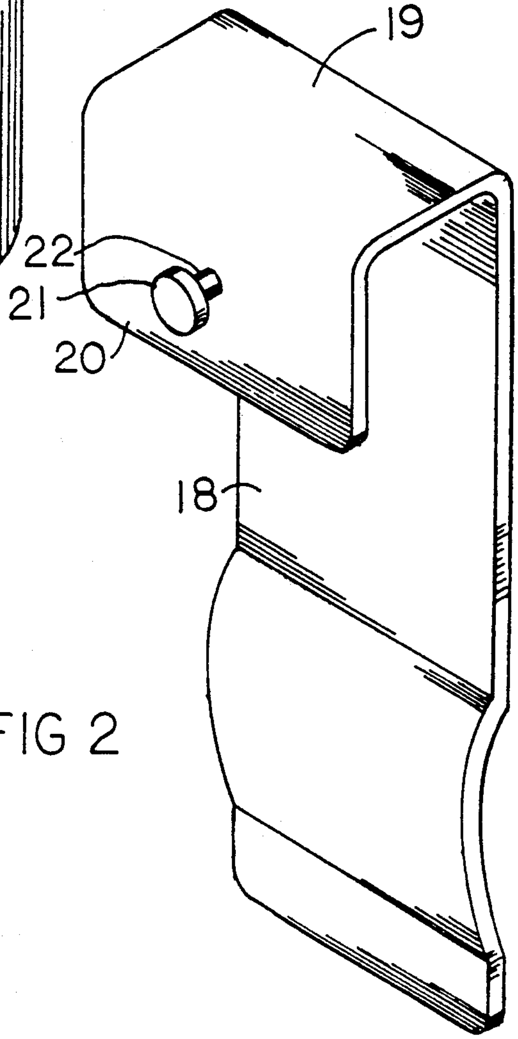
FIG. 2 is an isometric illustration of the bracket of the invention.

With reference now to the drawings, and in particular to FIGS. 1 to 8 thereof, a new and improved beverage container apparatus embodying the principles and concepts of the present invention and generally designated by the reference numeral 10 will be described.

More specifically, the beverage container 10 of the instant invention essentially comprises a cylindrical container 11 formed with a container lid 12 selectively securable to an upper distal end of the container to receive a drinking fluid therewithin. A conduit receiving boss 13 is mounted fixedly to the container to secure a drinking conduit 14 through the boss 13 into the container. A vent 15 is mounted to the container lid preventing of fluid during drinking from the container. An "L" shaped bracket 16 is mounted fixedly to an exterior wall of the container, including a slot spaced from and parallel the side wall of the container defined by a predetermined width. The slot is arranged for reception of a mounting head 21 secured to an outer distal end of a support rod 22 that in turn is orthogonally secured to a forward plate 20. The forward plate 20 includes an orthogonally mounted top plate 19 mounted to the inner portion of the forward plate, with the support plate 18 extending downwardly relative to the forward plate arranged in a generally parallel relationship relative to the forward plate to permit reception of a door and the like within a gap defined between the forward plate 20 and the support plate 18. The mounting head 21 is defined by a predetermined first diameter greater than a predetermined width defined by the slot 17 to permit securement of the "L" shaped bracket 16 relative to the forward plate 20 in use.

Figure 3:
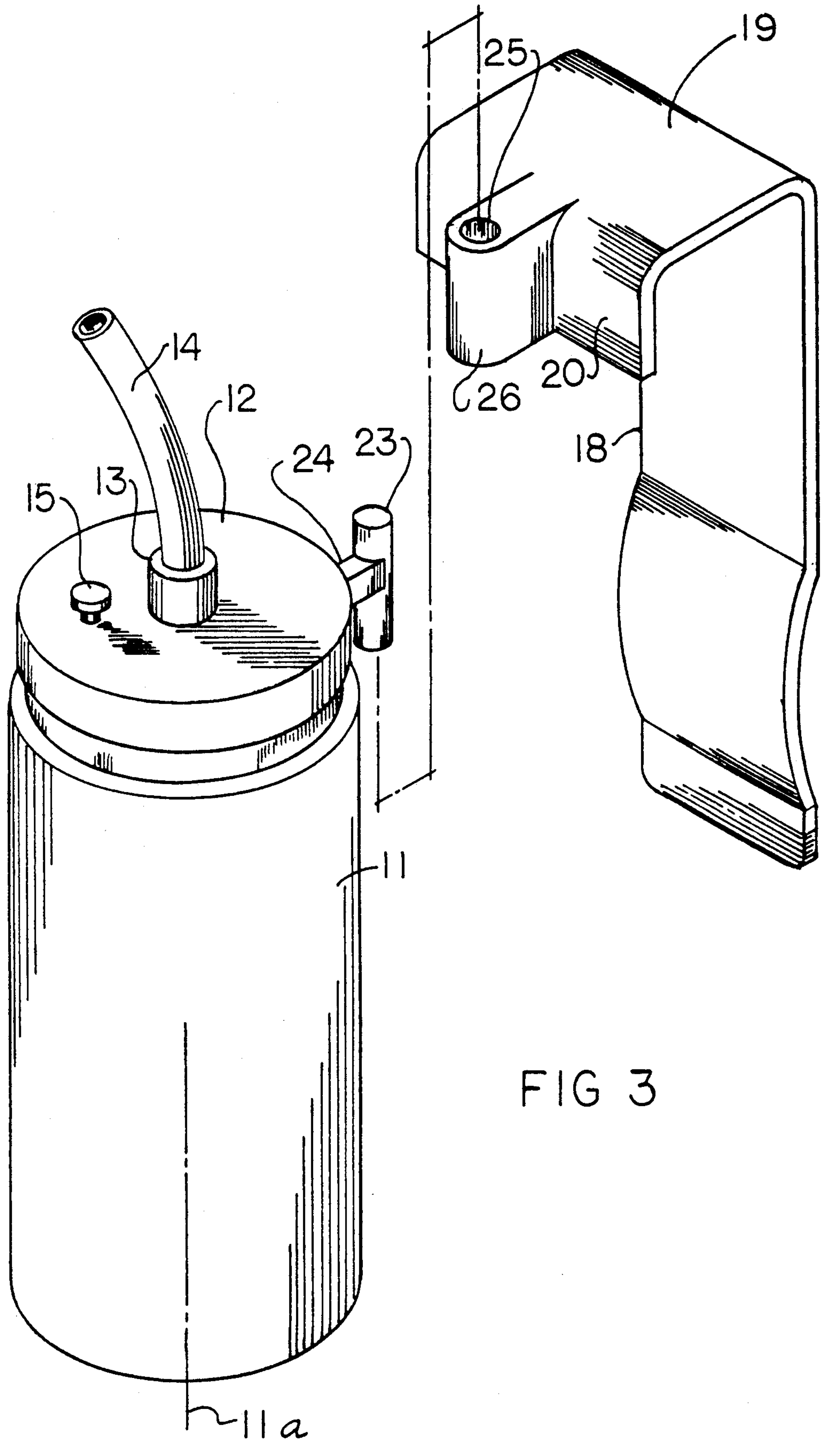
FIG. 3 is an isometric illustration of a further container and bracket structure utilized by the invention.

The cylindrical container 11, as illustrated in FIG. 3, includes a mounting cylinder 23 arranged in a parallel relationship relative to a cylindrical axis 11*a* defined by the cylinder, with a mounting cylinder rod 24 orthogonally mounted to the mounting cylinder 23 and to a periphery adjacent the upper distal end of the container 11. The forward plate 20 includes a mounting cylinder boss 26 extending orthogonally and forwardly thereof formed with a mounting cylinder receiving bore 25 directed coextensively through the boss oriented in a parallel relationship relative to the forward plate 20. The receiving bore 25 is thereby arranged to receive the mounting cylinder 23 therewithin.

Figure 4:
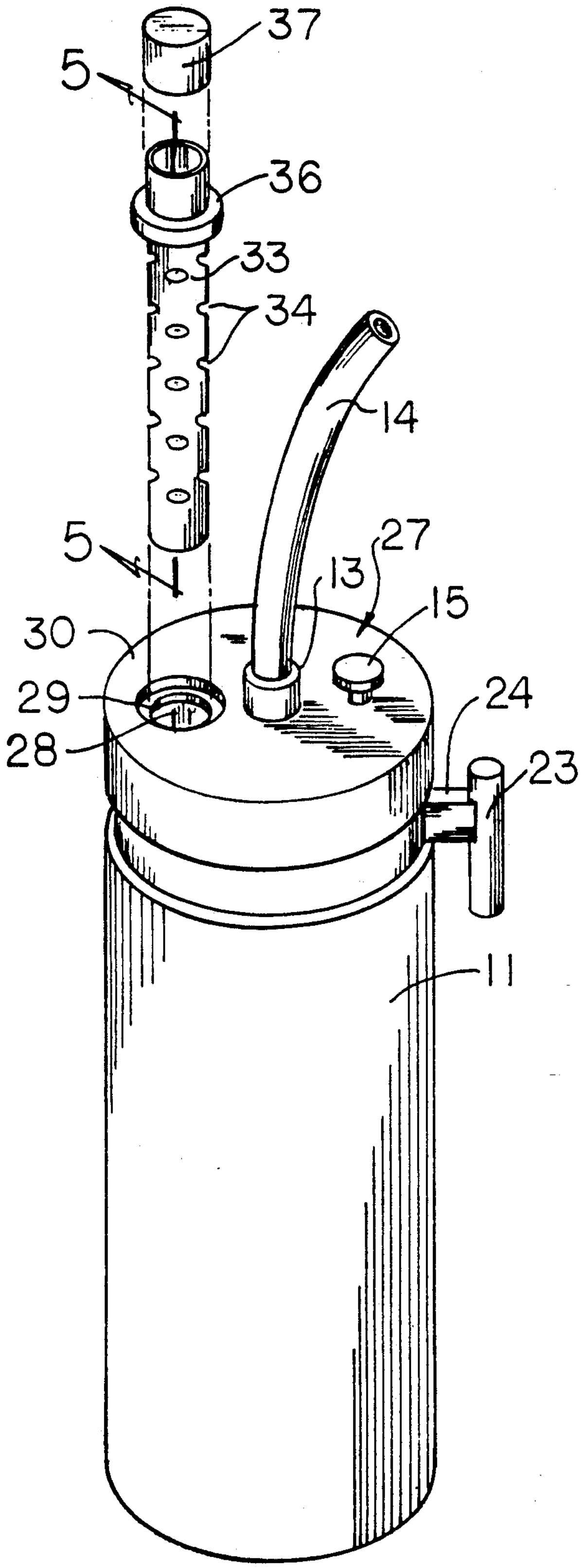
FIG. 4 is an isometric illustration of a modified container lid structure utilized by the invention.
Figure 5:
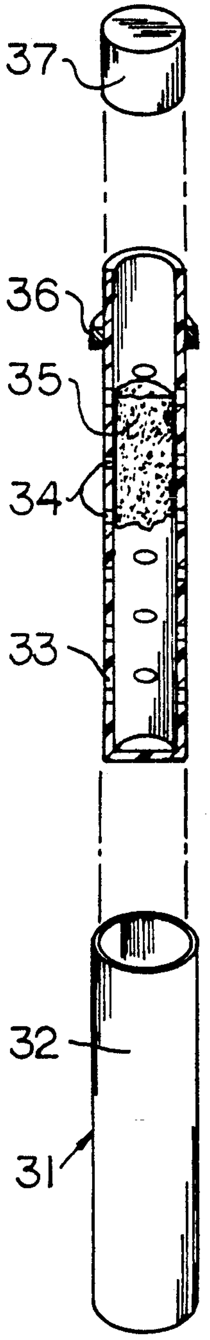
FIG. 5 is an exploded isometric illustration of a nutrient cylinder utilized by the invention.

The FIG. 4 illustrates the use of a modified lid 27 secured to the cylindrical container 11, wherein the modified lid 27 includes a modified lid bore 28 directed through the lid formed with a bore flange 29 spaced from a lid top surface 30. The flange 29 is of a generally cylindrical configuration arranged for reception of a nutrient cylinder 33 through the lid bore 28. The nutrient cylinder 33 includes a removable cylindrical protective sleeve 32 receiving a nutrient cylinder during periods of non-use for storage of the nutrient cylinder, whereupon removal of the nutrient cylinder relative to the sleeve 32 permits the exposure of a nutrient fluid contained within a saturated sponge 35 within the nutrient cylinder 33 to be directed into a fluid within the container 11. The cylinder includes a matrix of apertures 34 directed through the cylinder to permit this inter-mixing of a nutrient fluid from the sponge 34. A magnetic collar 36 fixedly mounted to the nutrient cylinder in a concentric relationship is spaced from an upper distal end of the nutrient cylinder to magnetically adhere a ferrous cap 37 to the upper distal end of the nutrient cylinder. Removal of the cap permits replenishment of the sponge with the aforenoted nutrient fluid.

Figure 7:
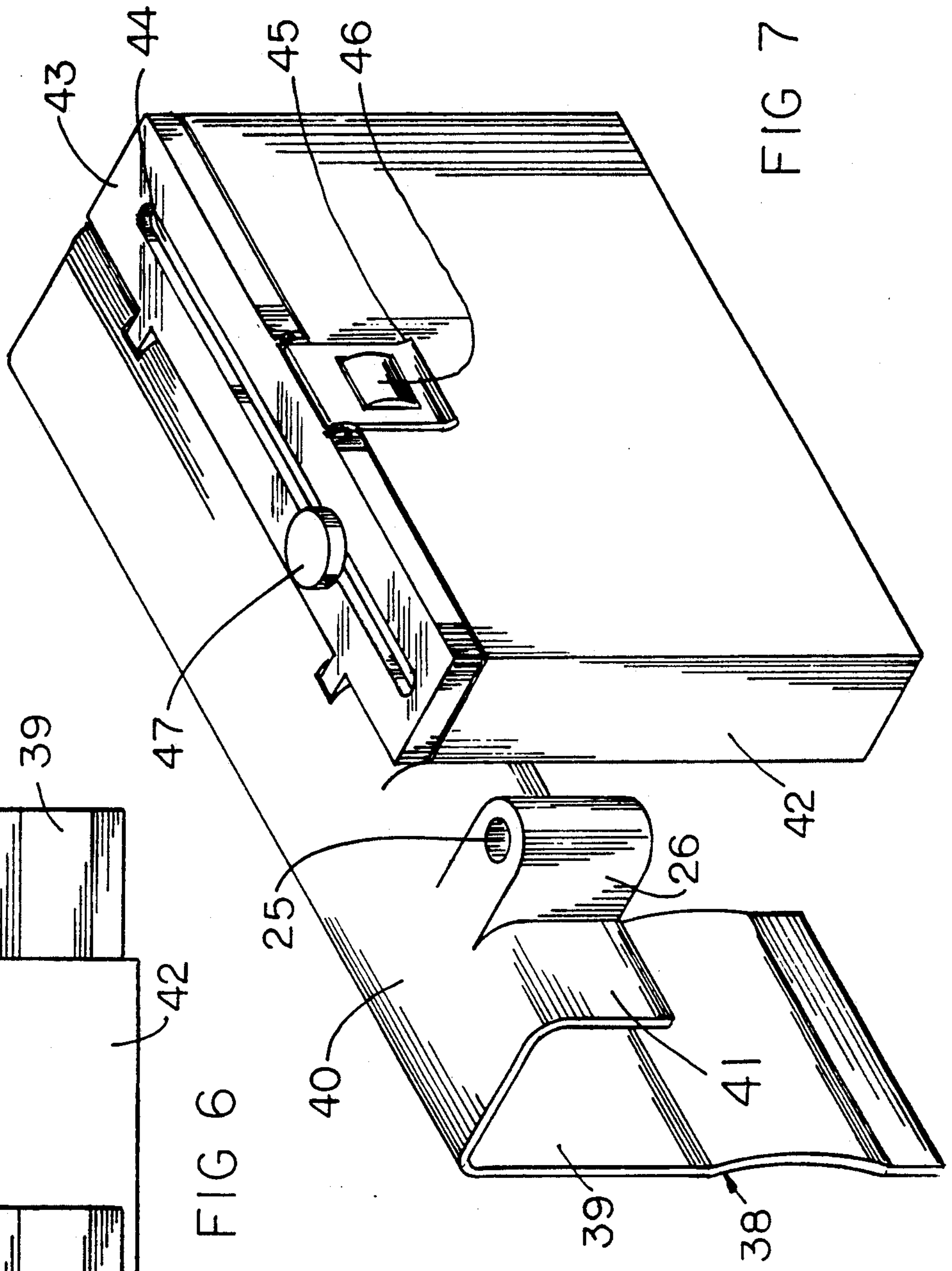
FIG. 7 is an isometric illustration of the support container structure for support of the nutrient cylinders.
Figure 6:
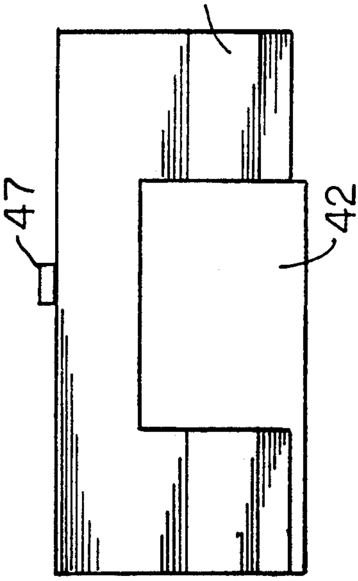
FIG. 6 is an orthographic rear view of a modified support structure utilized for the support of the container and nutrient cylinders of the invention.
Figure 8:
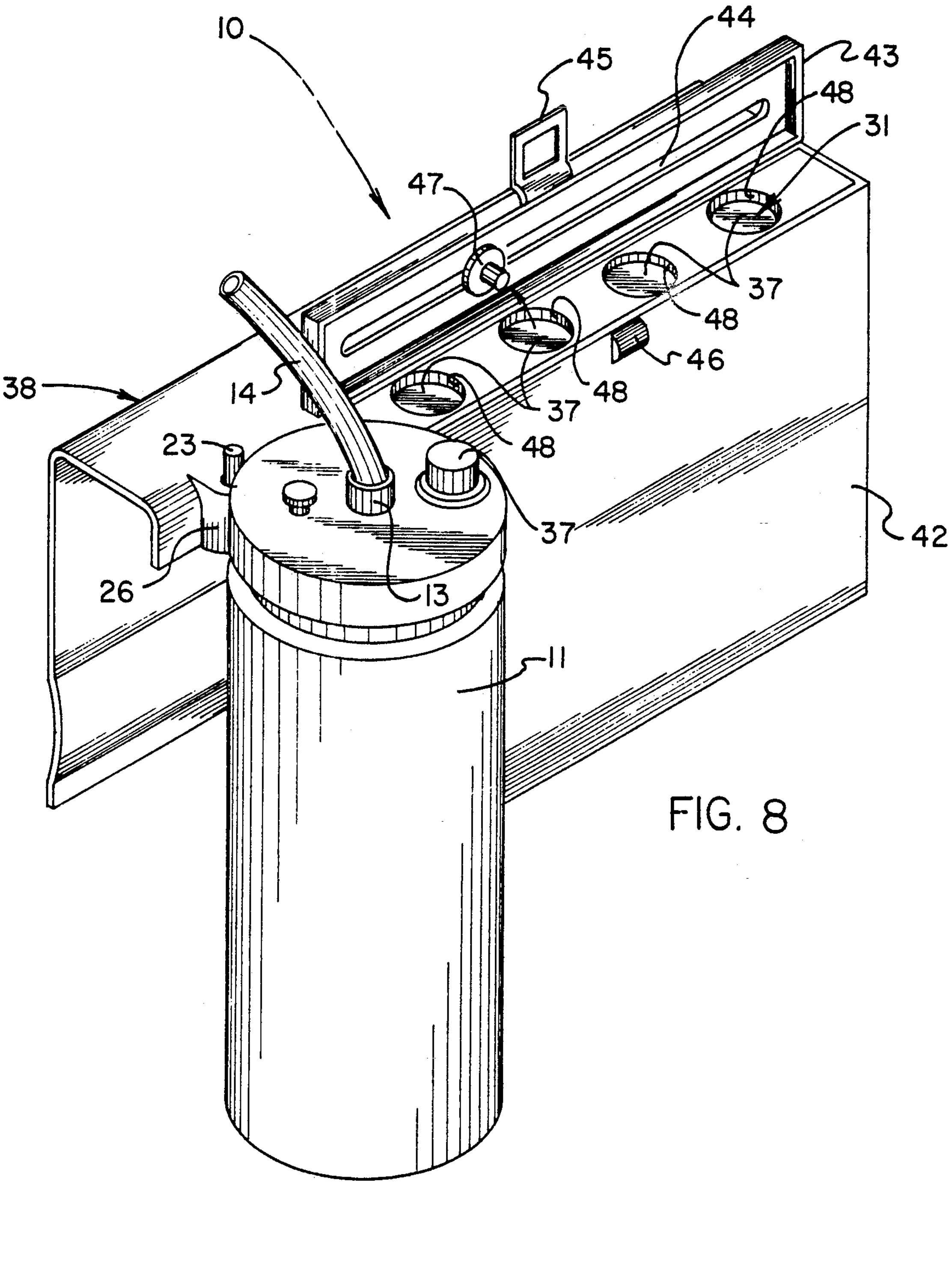
FIG. 8 is an isometric illustration of the invention in combination relative to one another.

The FIGS. 6–8 illustrate the use of a support bracket 38 utilized in combination with a plurality of nutrient cylinders that are stored within an associated support container 42. The bracket 38 includes a first plate 39 to include a second plate 40 orthogonally mounted to an upper distal end of the first plate, with a third plate 41 orthogonally mounted extending downwardly relative to the second plate, wherein a third plate 41 is arranged in a parallel spaced relationship relative to the first plate to permit reception of a belt loop or a vehicular portion such as a door frame within a window within the spacing defined between the third plate 41 and the first plate 39. The support container 41 is mounted fixedly to the third plate 41, with a lid 43 pivotally mounted to the support container 42 adjacent the third plate 41. A latch strap 45 with a lid 43 is securable to a latch boss 46 mounted to a front wall of the support container 42. The support container lid 43 includes an enclosed slot 44 directed therethrough, with the slot 44 including a magnetic slide 47 slidably directed along the slot, with the container including a series of spaced vertical walls 48, each including a nutrient cylinder and its associated sleeve therewithin. The ferrous cap 38 is accordingly cooperative with the magnetic slide 47, whereupon lifting of the lid and the slide positioned above a chosen well effects magnetic adhesion of the slide 47 to the ferrous cap 37 of a nutrient cylinder contained within that chosen well permitting initial lifting of the nutrient cylinder relative to the well for ease of manual grasping and subsequent insertion into the lid structure, as set forth in FIG. 4.

In this manner, nutrient fluids such as vitamin supplements and the like may be added at intervals in association with the fluid for use by athletes and the like. Alternatively, medicines may be directed into the drinking fluid within the container 11 for consumption by individuals.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A beverage container apparatus, comprising, a cylindrical container, the cylindrical container including a container lid securable to an upper distal end of the cylindrical container, the cylindrical container arranged for reception of a drinking fluid therewithin, with the lid including a conduit receiving boss fixedly mounted to the lid and a drinking conduit received through the boss for reception within the fluid, and the container defined about a container axis, and a mounting cylinder rod fixedly secured to the container adjacent said upper distal end of the container orthogonally oriented relative to the axis, with the rod fixedly and orthogonally mounted to a mounting cylinder, the mounting cylinder extending below the rod, and a first plate, the first plate including a second plate connected to the first plate in an orthogonal relationship extending forwardly of the first plate, and a third plate extending downwardly from the second plate arranged parallel to the first plate, wherein the third plate includes a mounting cylinder boss fixedly secured to the third plate extending forwardly thereof, and a mounting cylinder receiving bore directed coextensively through the mounting cylinder boss, wherein the mounting cylinder receiving bore is arranged for reception of the mounting cylinder therewith, and the lid includes a lid bore directed therethrough, the lid bore including a bore flange arranged about the lid bore in an encircling peripheral relationship, with the lid including a top surface and the flange positioned below the top surface, and at least one nutrient cylinder, the nutrient cylinder including a sleeve selectively and slidably receiving the nutrient cylinder therewithin, and the nutrient cylinder including a magnetic collar mounted to the nutrient cylinder adjacent an upper distal end of the nutrient cylinder, wherein the magnetic collar includes a ferrous cap selectively secured to said upper distal end of the nutrient cylinder adhered to the magnetic collar, and the nutrient cylinder including a nutrient fluid saturated sponge contained within the nutrient cylinder, the nutrient cylinder including a matrix of apertures directed therethrough, and the nutrient cylinder arranged for projection through the lid bore, with the magnetic collar arranged for mounting upon the bore flange.

2. An apparatus as set forth in claim 1 wherein the third plate includes a support container mounted to the third plate spaced from the mounting cylinder boss, with the support container including a support container lid pivotally mounted to the support container, the lid including an enclosed slot directed through the support container lid, and the lid slot including a magnetic slide slidably received within the lid slot, and the support container including a plurality of cylindrical wells positioned within the support container under the container lid, and each of the wells including a further nutrient cylinder container therewithin, with each nutrient cylinder including a ferrous cap positioned adjacent an upper distal end of each well, with the magnetic slide arranged for magnetic attraction to a selective one of said ferrous caps upon orientation of the magnetic slide above a selected one of said cylindrical wells.

* * * * *